United States Patent [19]

Vives et al.

[11] 4,267,351

[45] May 12, 1981

[54] SULFUR TRIOXIDE ADDUCTS OF SULFOLENES

[75] Inventors: Van C. Vives; John E. Mahan, both of Bartlesville, Okla.

[73] Assignee: Phillips Petroleum Company, Bartlesville, Okla.

[21] Appl. No.: 133,721

[22] Filed: Mar. 25, 1980

Related U.S. Application Data

[62] Division of Ser. No. 944,958, Sep. 22, 1978, abandoned.

[51] Int. Cl.$^3$ ............................................ C07D 333/00
[52] U.S. Cl. ...................................... 549/19; 252/121; 252/532; 549/67
[58] Field of Search .................................... 549/19, 15

[56] References Cited

PUBLICATIONS

Pavlov et al., Khimiya Geterotsiklicheskikh Soedinenii, vol. 3, pp. 306 to 309, (1972).
Texaco Dev. Corp., Chem. Abstracts, vol. 44, col. 3030 d–i (1950), (abst. of Brit. 627,247).
Pavlov et al., Chem. Abstracts, vol. 77, abst. 61855u, (1972).
Chemical Abstracts, 9th Collective Subject Index, p. 37358CS, (copyrighted 1968), American Chemical Society.
Breslow et al., Multi-Sulfur and Sulfur and Oxygen Five- and Six-Membered Heterocycles, Part Two, pp. 611 to 623, Interscience Publishers NY (1966).
Molony et al., Chem. Abstracts, vol. 57, col. 10120 (1962).

*Primary Examiner*—John D. Randolph

[57] ABSTRACT

Cyclic sulfonate-sulfate anhydrides are produced by the reaction of an α- or β-type sulfolene compound with $SO_3$. Reaction of the cyclic sulfonate-sulfate anhydrides with alcohols produces alkyl esters of hydroxysulfolane sulfonic acids. The cyclic sulfonate-sulfate anhydrides or the alkyl esters of hydroxysulfolane sulfonic acids can be hydrolyzed to hydroxysulfolane sulfonic acids or their respective salts. The latter can be acylated to alkylcarbonyloxysulfolane sulfonic acids.

5 Claims, No Drawings

SULFUR TRIOXIDE ADDUCTS OF SULFOLENES

This is a divisional application of Ser. No. 944,958 filed Sept. 22, 1978, now abandoned.

FIELD OF INVENTION

The invention pertains to cyclic sulfonate-sulfate anhydrides (carbyl sulfates). In another aspect, the invention pertains to alkyl esters of hydroxysulfolane sulfonic acids. In another aspect, the invention pertains to hydroxysulfolane sulfonic acids and their respective salts. In a further aspect, the invention pertains to alkylcarbonyloxysulfolane sulfonic acids. In an additional aspect, the invention pertains to surface-active agents.

BACKGROUND OF THE INVENTION

Surface-active agents are compounds that usually function by reducing the surface tension of aqueous solutions or reducing the interfacial tension between two liquids. Surface-active agents are generally referred to as anionic, cationic, or nonionic. Such agents are useful as detergents, wetting agents, penetrants, dispersing agents, foaming agents, and the like. The search for novel effective surface active agents continues, particularly in the area of nonionic surface-active agents which are considered most desirable in aqueous media since they are not affected or at most only slightly affected by the concentration of various salts in the aqueous media.

BRIEF DESCRIPTION OF THE INVENTION

We have discovered novel cyclic sulfonate-sulfate mixed anhydrides, which also can be termed carbyl sulfates, and have found that they are useful in preparing novel alkyl esters of hydroxysulfolane sulfonic acids useful as nonionic surface-active materials. The cyclic sulfonate-sulfate anhydrides, or the alkyl esters of hydroxysulfolane sulfonic acids, can be hydrolyzed to hydroxysulfolane sulfonic acids or their salts. The latter, on acylation, are converted to alkylcarbonyloxysulfolane sulfonic acids, also useful as anionic surface active agents.

DETAILED DESCRIPTION OF THE INVENTION

Cyclic Sulfonate-Sulfate Anhydrides

The cyclic sulfonate-sulfate anhydrides or carbyl sulfates in accordance with one aspect of our invention can be represented by any of:

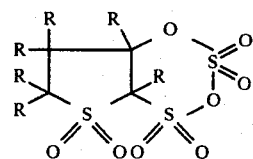

(I)

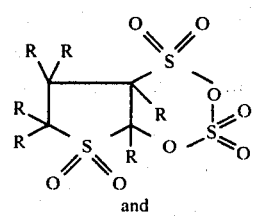

(II)

and

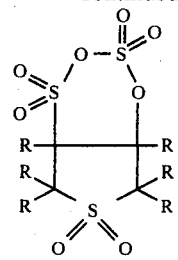

(III)

In the generic formulae (I), (II), and (III) for the cyclic sulfonate-sulfate anhydrides, each R is individually selected from either a hydrogen atom or a hydrocarbon radical. Each hydrocarbon radical can be selected from alkyl, cycloalkyl, aryl, aralkyl, and alkaryl hydrocarbon groups. The size of one or more R groups does not appear limited as far as operability is concerned, but presently for convenience and availability R should be such that the number of carbon atoms in the cyclic sulfonate-sulfate anhydrides of our invention is in the range of such as 4 to 32, more preferably 4 to 8, and most preferred are those structures in which each R is hydrogen and the cyclic sulfonate-sulfate anhydrides thus contain 4 carbon atoms per molecule.

In preparation of our cyclic sulfonate-sulfate anhydrides, an α or β-sulfolene-type compound is reacted with effective amounts of sulfur trioxide under effective reaction conditions of temperature, pressure, time and including use of a suitable reaction solvent. Carbyl sulfates as represented by formulae (I) and (II) above result from the use of an α-sulfolene, and by formula (III) from the use of a β-sulfolene, as starting material.

The term "sulfolene-type compound" is used by us to define both the α-sulfolene type compounds and the β-sulfolene type compounds, which can be represented respectively by the formulae:

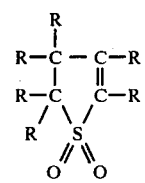 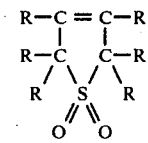

(α) ; and (β)

The sulfolene nucleus can have various hydrocarbon radicals attached thereto as substituents. In the above (α) and (β) formulae, each R is as previously described.

Sulfolene-type compounds typically include such as α-sulfolene, β-sulfolene, 3-methyl-2-sulfolene, 2-methyl-3-sulfolene, 3-methyl-3-sulfolene, 2,4-dimethyl-2-sulfolene, 2,4-dimethyl-3-sulfolene, 3-ethyl-3-sulfolene and their homologs, as well as other sulfolene compounds in which hydrocarbon radicals, such as methyl, ethyl, propyl, isopropyl, butyl, isobutyl, amyl, hexyl, isohexyl, cyclohexyl, phenyl, benzyl, xylyl and other like radicals substitute for one or more of the hydrogen atoms of the suflolene compounds.

The sulfur trioxide can be employed as such in a solid, liquid, or gaseous state. Preferably and conveniently, the sulfur trioxide can be employed in the form of a solution, such as $SO_3$ in dichloromethane. Other suitable solutions include $SO_3$ in liquid $SO_2$, in dichloroethane, or in sulfuric acid. In the gaseous state, $SO_3$ is advantageously diluted with another gaseous material such as dry air, nitrogen, or SO₂. The sulfur trioxide also can be employed in the form of its addition compounds with sulfolane, dioxane, or pyridine.

The molar ratio of $SO_3$ to sulfolene compound should be suitable and effective to result in the reaction described, and can vary over a broad range. An exemplary range of about 0.1:1 to 5:1, presently preferred about 1:1 to 3:1, is recommended in practice. Two mols of $SO_3$ are equivalent to one mol of sulfolene compound based on stoichiometry regardless of the initial molar quantities of reactants used. Thus, for economic reasons molar ratios of $SO_3$ to sulfolene exceeding 5:1 are not considered desirable because of the relatively large amounts of unreacted $SO_3$ which must be separated for recycle and/or possibly lost in the operation. Thus, in practice, it is considered desirable to employ approximately 2 mols of $SO_3$ for each mol of sulfolene.

The process can be carried out over broad temperature range, so long as effective for the reaction. A suitable exemplary temperature range is about $-70°$ C. to $+70°$ C., with a presently preferred temperature range of about 0° C. to 50° C. Moderate temperatures are preferred and reasonable reaction rates are observed even at ambient temperature. Higher temperatures are not desirable because of the possibility of thermally cleaving the sulfolene nuclear moiety to alkadiene and $SO_2$. Any suitable pressure can be employed, though preferable and convenient are pressures sufficient to maintain the reactants in essentially a liquid state. Total reaction time can vary widely, such as over about 10 minutes to 24 hours, preferably one to four hours.

The preparation of our cyclic sulfonate-sulfate anhydrides is advantageously carried out under a reaction-inert atmosphere such as nitrogen though other gaseous materials substantially inert under the reaction conditions, such as helium, argon, and the like, can be employed to protect the system from atmospheric oxygen and moisture.

Solvents employed in the reaction process, of course, must be inert under the reaction conditions. Suitable solvents can be selected from halogenated aliphatic hydrocarbons such as dichloromethane, dichloroethane, chloroform, carbon tetrachloride, and the like as well as ethers such as dioxane, tetrahydrofuran, diethyl ether, and the like. Sulfolane, which forms a complex with $SO_3$, conveniently can be used as solvent and/or as a source of $SO_3$.

The sulfonation product reaction mixtures can be worked up in conventional manners. In general, the entire reaction mixture can be concentrated to a crude residue by use of evaporative means such as a rotary evaporator at aspirator pressure to remove volatiles. The last traces of $SO_3$ and/or solvent can be removed by passing a gaseous material such as nitrogen over the residue. Any unreacted sulfolene can be extracted from the residue by the use of a suitable solvent such as dichloromethane or a solvent mixture such as cyclohexane/benzene to leave the inventive compositions as a tractable material which then can be further purified as necessary or as desired by such as recrystallization from a solvent mixture such as hexane/dichloromethane.

The cyclic sulfonate-sulfate anhydrides are useful as intermediates in the formation of alkyl esters of hydroxysulfolane sulfonic acids, in the formation of alkylcarbonyloxy hydroxysulfolane sulfonic acids or their salts, and also will find useful applications in extractive distillation processes particularly with other solvents.

Alkyl Esters of Hydroxysulfolane Sulfonic Acids

In accordance with another aspect of our invention, the cyclic sulfonate-sulfate anhydrides are reacted under effective reaction conditions of temperature, pressure, and time, with effective amounts of an alkanol to prepare alkyl esters of hydroxysulfolane sulfonic acids which we have found to be effective nonionic surface-active materials.

The alkyl esters of hydroxysulfolane sulfonic acids are unusual in that they contain dual-$SO_2$-groups. These products also contain a hydroxy function, as well as a hydrocarbon chain which can be of variable length. This character, though we do not wish to be bound by theoretical considerations, may assist in their unique surface-active character. The side chain characteristic, particularly where long hydrocarbon chain, provides hydrophobic character, while the dual-$SO_2$-groups and the —OH groups provide hydrophilic character. These structural aspects provide a multifunctional character to the products making them useful as surface-active agents.

These alkyl esters of hydroxysulfolane sulfonic acids can be represented by the formulae:

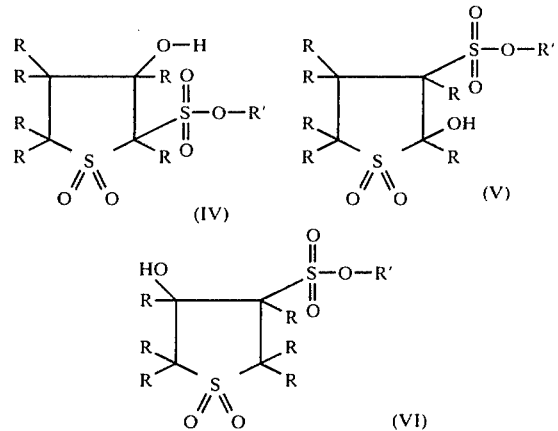

In the formulae (IV), (V), and (VI) above for the alkyl esters of hydroxysulfolane sulfonic acids each R is as defined above. R' is an alkyl (hydrocarbon) radical and is not considered limited in operability by a number of carbon atoms. However, for convenience and availability, R' alkyl radicals of 6 to 20 carbon atoms are suggested, presently preferred are those of 7 to 16 carbon atoms, and most preferred are those of 7 to 12 carbon atoms. If the R' group is too short, insufficient hydrophobic character may result. If the R' is excessively long, the overall solubility/dispersability of the resultant ester may be adversely affected.

The alkyl esters of hydroxysulfolane sulfonic acids are prepared by reaction of one or more of the cyclic sulfonate-sulfate anydrides with one or more appropriate alkanols. Typical alkanols suitable in accordance with our invention are heptanol, hexanol, dodecanol, octadecanol, eicosanol, hexadecanol, and the like, alone or in admixture. Of course, mixtures of alcohols can be employed, and frequently are convenient, since most economically available commercial alcohols represent a mixture of two or more species or isomers.

The alkyl esters of hydroxysulfolane sulfonic acids as represented by formula (VI) above result from the reaction of a cyclic sulfonate-sulfate anhydride of formula (III) with a suitable alkanol. The alkyl esters of hydroxysulfolane sulfonic acids represented by formulas (IV) and (V) above result from the reaction of a cyclic sulfonate-sulfate anhydride of formula (I) or (II) above, with the resulting preponderance of one or the other of (IV) or (V) dependent primarily on the nature of the R group substituents.

It is not necessary to separate mixed products, since the resultant product is highly effective nonionic surface-active material. However, if a pure or substantially pure material is desired, such can be separated by preparative chromatography, fractional distillation, fractional crystallization, or the like.

In preparing the alkyl esters of hydroxysulfolane sulfonic acids, the desired cyclic sulfonate-sulfate anhydride is reacted with an alkanol or alkanols by contacting the two components either in the pure state or in a suitable solvent system.

Any suitable effective ratio of alkanol to cyclic sulfonate-sulfate can be employed, since excess material can be recycled where desired after separation from the reaction product mixture. If desired, the sulfonate-sulfate anhydride can first be hydrolyzed with water to form the hydroxysulfonic acid, followed by esterification with alcohol. A suggested ratio is about 0.5:1 to 25:1 molar ratio alcohol:cyclic sulfonate-sulfate or hydroxysulfonic acid, presently preferred is about 2:1 to 5:1.

Suitable solvents include halogenated alkanes, such as dichloromethane, dichloroethane, and chloroform; and ethers such as dioxane, tetrahydrofuran, diethyl ether; and the like; alone or in admixture. The reaction can be conducted conveniently in the presence of excess alkanol without employing an additional solvent. This aspect can be desirable and a convenience since it avoids introducing an extraneous material into the system which ultimately must be separated.

The reaction of the cyclic sulfonate-sulfate anhydride with the alkanol can be conducted over any suitable broad temperature range. A suitable exemplary temperature range is about $-20°$ C. to $+150°$ C., presently preferred about $+20°$ C. to $+120°$ C. Moderate temperatures are preferred, and reasonable reaction rates are observed even at ambient temperatures. Higher temperatures are not desirable in this aspect of our process because of the possibility of thermally decomposing the ring moiety. The reaction can be conducted at any convenient pressure, though preferably at a pressure sufficient to maintain the reactants substantially in the liquid phase. The reaction can be conducted as convenient in any suitable reactor, of course with suitable stirring and agitation.

After a suitable reaction time, such as about 2 to 4 hours, the product stream can be treated for recovery by conventional means. The product stream effluent can be concentrated by vacuum treatment, followed by extraction, crystallization, recrystallization, and the like, for recovery of the alkyl esters of hydroxysulfolane sulfonic acid. While separation of pure alkyl esters of hydroxysulfolane sulfonic acids can be conducted if desired, use of mixtures for most commercial surface-active applications is suitable.

Hydroxysulfolane Sulfonic Acids

In accordance with a further aspect of our invention, the cyclic sulfonate-sulfate anhydrides or the alkyl esters of hydroxysulfolane sulfonic acids can be hydrolyzed to either hydroxysulfolane sulfonic acids.

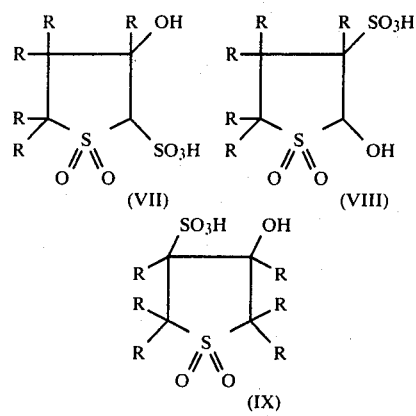

or to their respective salts, depending on whether water or aqueous base, such as dilute sodium hydroxide, is used in the hydrolysis.

In the above formulae, R is as previously defined.

Any of the cyclic sulfonate-sulfate anhydrides or alkyl esters of hydroxysulfolane sulfonic acids can be employed, alone or in admixture. Hydrolysis of the anhydrides or esters is conducted under hydrolysis conditions with water and preferably dilute alkaline hydroxide at a suitable temperature of such as about 40° to 100° C. for a time suitable to form the corresponding hydroxysulfolane sulfonic acids, such as by hydrolysis with dilute alkali, followed by neutralization with acid, and recovery of the hydroxysulfolane sulfonic acids. The free acid is hygroscopic and so is most conveniently handled as the sodium salt or other alkali metal salt.

Alkylcarbonyloxysulfolane Sulfonic Acids

Any one or more of the hydroxysulfolane sulfonic acids can be reacted with an acid halide in an acylation reaction under acylation conditions to produce alkylcarbonyloxysulfolane sulfonic acids:

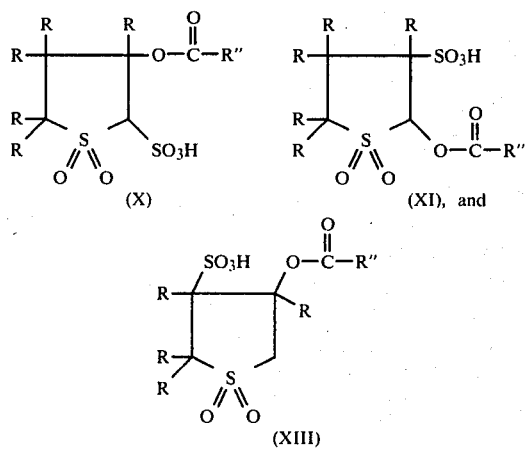

in which R is as previously defined. These materials have the characteristics useful as anionic surface-active materials, particularly as the alkali metal salt, such as sodium, with detergent effectiveness. In the acid halides

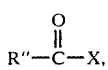

R″ is alkyl R′, or substituted alkyl, and where substituted alkyl is alkaryl or aralkyl of 12 to 20 carbon atoms. R′ is as previously described. Where R″ is a substituted alkyl, the alkaryl group can be such as dodecylphenyl, octylphenyl, hexylphenyl, and the like or the aralkyl group can be such as phenyldodecyl, phenylhexyl, phenyloctyl, and the like. Presently preferred is dodecylphenyl. X is a halide, preferably and usually chloride.

EXAMPLES

The following examples are intended to assist one skilled in the art to a further understanding of our invention. Particular species, reactants, conditions, amounts, and the like, are all intended to be exemplary of our invention, and not limitative thereof, but rather as exemplification of and as a further portion of our overall disclosure.

EXAMPLE I

A charge of 7 g (0.059 mol) of β-sulfolene and 600 ml dichloromethane was placed in a 3-necked, 1-liter reaction flask fitted with a nitrogen inlet and outlet, magnetic stirrer, and rubber septum. The stirred reaction mixture was cooled to −68° C. in a dry ice/acetone bath during the addition of 15.2 g (7.4 ml, 0.189 mol) of liquid sulfur trioxide by means of a syringe over a period of 11.5 minutes. The cloudy reaction mixture was maintained at about −68° C. for an hour and then became clear on slowly warming to room temperature. After an additional two hours at ambient temperature, white crystals were observed on the walls of the flask and the mixture was maintained at room temperature under a nitrogen atmosphere for approximately 24 hours before work-up. Excess SO₃ and dichloromethane were removed at aspirator vacuum to yield a white solid residue containing traces of dark brown flecks and a small amount of oil. A stream of nitrogen was passed over the residue to remove the last traces of SO₃ and this treatment was followed by extraction of residual β-sulfolene with 1:1 cyclohexane/benzene. The crude solid reaction product turned tan in color after standing overnight under a nitrogen atmosphere. The crude product weighed 16.3 g corresponding to a weight gain of 9.3 g (0.116 mol) SO₃. This represents a 1.96:1 molar ratio of SO₃ to β-sulfolene in the crude product.

The above product was characterized by observing its behavior on reaction with aqueous sodium hydroxide. A 0.6068 g sample of the above product was neutralized with 44.4 ml of 0.0961 N sodium hydroxide which is equivalent to 0.00427 mol. Thus, the mol ratio of base to sample was 1.96:1 which agreed with the ratio of SO₃ to β-sulfolene based on the weight gain cited above.

An additional 0.595 g sample of the above product was added to excess 0.1 N sodium hydroxide solution and the mixture was heated at 50°–65° C. for a period of 16 hours. The solution was cooled to room temperature and the excess base was titrated with 0.1 N HCl to establish that the base consumed prior to the back-titration indicated a 3:1 molar ratio of base to sample. These observations suggest that the following sequence of events take place on treating the 62-sulfolene/SO₃ adduct with NaOH.

(1) NaOH Titration Step

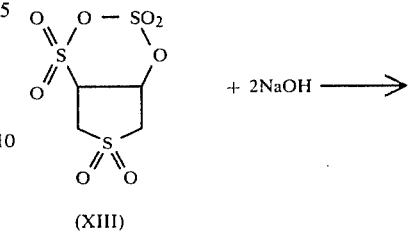

(2) Excess NaOH and Heat

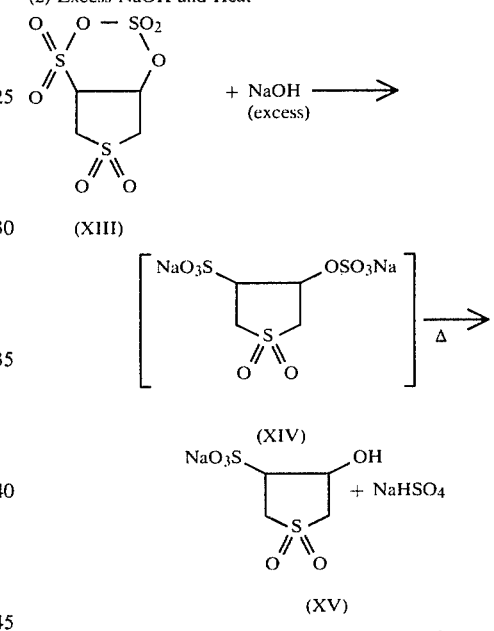

$NaHSO_4 + NaOH \longrightarrow Na_2SO_4 + H_2O$

Acidification of compound XV results in the free sulfonic acid. The yield of crude SO₃ adduct was 99% and the conversion of β-sulfolene was about 100%. Infrared spectral analysis (KBr): 2.8, 3.3, 3.4, 5.1-6.3 (broad), 6.9, 7.05, 7.5, 7.7, 8.0, 8.1, 8.4, 8.65, 8.8, 9.5, 9.8, 10.4, 10.8, 12.2-13.2, 13.6, 14.0, 14.5μ. An elemental analysis of the product gave the following results: Calcd. for $C_4H_6S_3O_8$: C, 17.26; H, 2.17; S, 34.57. Found: C, 16.92; H, 2.36; S, 30.0.

EXAMPLE II

A charge of 7 g (0.059 mol) of α-sulfolene and 600 ml dichloromethane was placed in a 3-necked, 1-liter reaction flask fitted with a nitrogen inlet and outlet, magnetic stirrer, and rubber septum. The stirred reaction mixture was cooled to −68° C. in a dry ice/acetone bath during the addition of 4.8 g (0.061 mol) of liquid sulfur trioxide by means of a syringe over a period of 4 minutes. The cloudy reaction mixture was maintained at about −68° C. for 2.75 hours and then became a clear homogeneous mixture on warming to ambient temperature. The mixture was maintained at room temperature for about 36 hours and a small amount of solid formed on the walls of the flask.

The reaction mixture was boiled under nitrogen for four hours, cooled to room temperature, and traces of $SO_3$ and solvent were removed at aspirator vacuum. A nitrogen sweep was used to remove the last trace of volatiles from the off-white solid residue which contained a small amount of oil. Treatment of this residue with dichloromethane gave 5.48 g of $CH_2Cl_2$-soluble oil. This oil was primarily unreacted α-sulfolene. The $CH_2Cl_2$-insoluble white solid weighed 5.02 g. A 0.2914 g sample of the solid required 30.5 ml of 0.0961 N NaOH (0.00293 mol) for neutralization, indicating that 3 moles of NaOH reacted with one mol of $SO_3$/α-sulfolene adduct. The white solid gave the following analysis: Calcd. for $C_4H_6S_3O_8$: C, 17.26; H, 2.17; S, 34.57; Found: C, 17.48; H, 2.51; S, 34.0. The elemental analysis is consistent with either of the structures:

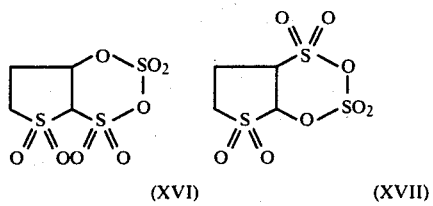

(XVI)          (XVII)

EXAMPLE III

A sample of the $SO_3$ adduct of β-sulfolene from Example I was heated with excess 1-heptanol in dichloromethane for several hours to effect solution. The yellow reaction solution was treated with decolorizing charcoal, and excess solvent and 1-heptanol were removed on a rotary evaporator. A solid residue containing oil was obtained. This residue was washed with hexane and an almost white insoluble solid was isolated. The infrared spectrum of this solid exhibited a sharp hydroxyl peak at 2.8μ with additional bands at 3.3, 3.4, 3.5, 6.9, 7.05, 7.4, 7.6, 7.8, 8.2, 8.6, 9.0, 9.4, 9.8, 10.2, 10.5, 10.75, 11.3, 12.4, and 13.0. A structure consistent with this analysis is:

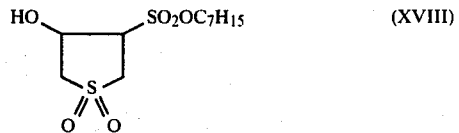

(XVIII)

The white solid was partially soluble in $CH_2Cl_2$. The residual sticky insoluble mass was discarded. The solution was treated with decolorizing charcoal and filtered. The filtrate was cooled to $-20°$ C. to yield 0.8 g of a white powder which melted to a colorless oil at 121°-122° C. A second crop of crystals weighing 0.3 g was obtained by adding hexane to the mother liquor and cooling to $-20°$ C. An elemental analysis on the first crop of crystals gave the following results which are consistent with the indicated structure. Calcd. for (XVIII) ($C_{11}H_{22}S_2O_6$): C, 42.02; H, 7.05; S, 20.40; O, 30.53, Found: C, 41.85; H, 7.04; S, 21; O (by difference), 30.11.

EXAMPLE IV

The above composition XVIII from Example III was tested for use as an emulsifying agent. A 7.5 milligram sample was placed in a 25 ml glass-stoppered graduated cylinder with 15 g deionized water and 1 ml toluene (Inventive Mixture A). A mixture of 15 g of water and 1 ml of toluene (Control Mixture B) was placed in another 25 ml graduated cylinder. The two cylinders were shaken vigorously for one minute and then allowed to stand at room temperature for the time intervals indicated below at which observations were made.

| Time Interval After Shaking Mixture | Observations | |
|---|---|---|
| | Inventive Mixture A | Control Mixture B |
| 1 minute | Top layer of foam; Water phase milky white | Two distinct layers; Water layer clear |
| 3 minutes | Top layer partially clear; water layer still white and opaque | Two clear layers |
| 60 minutes | Water layer less opaque | Two clear layers |
| 150 minutes | Slight cloudiness in water layer | Two clear layers |

The above observations indicate that the inventive composition possesses the ability to promote the emulsification of toluene and water.

The disclosure, including data, illustrate the value and effectiveness of our invention. The examples, the knowledge and background of the field of the invention and general principles of chemistry and other applicable sciences, have formed the bases from which the broad descriptions of the invention including the ranges of conditions and the generic groups of operant components have been developed, which have formed, then, the bases for our claims here appended.

We claim:

1. Cyclic sulfonate-sulfate anhydrides represented by

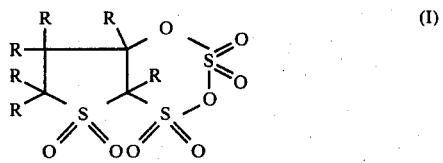

(I)

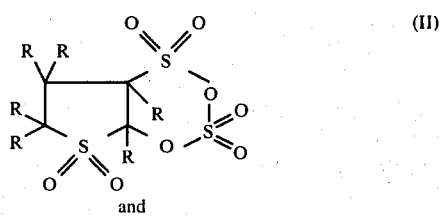

(II)

and

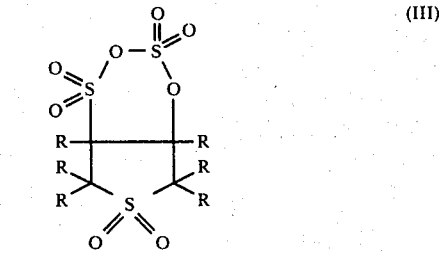

(III)

in which each R is individually selected from hydrogen and alkyl, cycloalkyl, aryl, aralkyl, and alkaryl hydrocarbon radicals.

2. Cyclic sulfonate-sulfate anhydrides according to claim 1 wherein R is hydrogen or a hydrocarbon radical of one to twelve carbon atoms, such that the total number of carbon atoms per cyclic sulfonate-sulfate anhydride is in the range of 4 to 32.

3. The cyclic sulfonate-sulfate anhydrides according to claim 2 wherein each R is hydrogen.

4. The cyclic sulfonate-sulfate anhydrides according to claim 3 wherein said cyclic sulfonate-sulfate anhydride is said (I), (II), or mixture.

5. The cyclic sulfonate-sulfate anhydrides according to claim 3 wherein said cyclic sulfonate-sulfate anhydride is said (III).

* * * * *